(12) United States Patent
Fabo et al.

(10) Patent No.: US 8,530,022 B2
(45) Date of Patent: Sep. 10, 2013

(54) ARTICLE OR COMPONENT OF A MEDICAL AND TECHNICAL NATURE FOR AFFIXING A MEDICAL ARTICLE OR PART THEREOF TO SKIN, PROVIDED WITH A RELEASABLE PROTECTION LAYER

(75) Inventors: Tomas Fabo, Mölnlycke (SE); Anna Svensby, Västra Frölunda (SE); Ulf Johannison, Landvetter (SE); Dennis Hansson, Gunnilse (SE)

(73) Assignee: Molnlycke Health Care AB (SE)

( * ) Notice: Subject to any disclaimer, the term of this patent is extended or adjusted under 35 U.S.C. 154(b) by 405 days.

(21) Appl. No.: 12/296,314

(22) PCT Filed: Mar. 14, 2007

(86) PCT No.: PCT/SE2007/050149
§ 371 (c)(1),
(2), (4) Date: Oct. 7, 2008

(87) PCT Pub. No.: WO2007/117208
PCT Pub. Date: Oct. 18, 2007

(65) Prior Publication Data
US 2009/0259192 A1    Oct. 15, 2009

(30) Foreign Application Priority Data
Apr. 11, 2006    (SE) ..................................... 0600808

(51) Int. Cl.
*B32B 3/30* (2006.01)
*B32B 7/02* (2006.01)
*B32B 7/04* (2006.01)
*B32B 7/06* (2006.01)
*B32B 7/12* (2006.01)
*A61F 13/02* (2006.01)
*B32B 3/28* (2006.01)
*B32B 7/10* (2006.01)

(52) U.S. Cl.
USPC .......... 428/41.7; 428/40.1; 428/41.3; 428/68; 428/76; 428/156; 428/166; 428/172; 428/332; 428/337; 428/339; 428/343; 428/354; 428/355 R; 602/54; 602/55; 602/57; 602/58

(58) Field of Classification Search
USPC ..................................... 602/54, 55, 57, 58, 41
See application file for complete search history.

(56) References Cited

U.S. PATENT DOCUMENTS 3,616,156 A * 10/1971 Scholl ........................... 428/163
3,944,692 A * 3/1976 Swenson ...................... 428/41.8

(Continued)

FOREIGN PATENT DOCUMENTS

EP    51935 A2 *  5/1982
EP    0300620       1/1989

(Continued)

OTHER PUBLICATIONS

Machine Translation of JP 2005171030 A, Jun. 2005.*

(Continued)

*Primary Examiner* — David Sample
*Assistant Examiner* — Jeff Vonch
(74) *Attorney, Agent, or Firm* — Ballard Spahr LLP

(57) ABSTRACT

An article (1) of a medical and technical nature intended to be affixed to skin, or a component for affixing a medical article or part thereof to skin, which article or component comprises a layer of carrier material (2) that has a layer (3) of a soft skin-friendly adhesive on one side, and a protection layer (4) that protects the adhesive layer before use of the article or component and is affixed to the adhesive layer in such a way that it is releasable. According to the invention, the protection layer (4) is provided with a pattern of projections (6) on the side facing towards the adhesive layer (3) and a reinforcing layer (5) is arranged on the layer of carrier material (2), on the opposite side to the side that has the layer of soft skin-friendly adhesive, in such a way that it can be removed.

18 Claims, 2 Drawing Sheets

(56) References Cited

U.S. PATENT DOCUMENTS

| | | | |
|---|---|---|---|
| 4,372,303 A * | 2/1983 | Grossmann et al. | 128/851 |
| 4,706,662 A * | 11/1987 | Thompson | 602/44 |
| 4,915,102 A * | 4/1990 | Kwiatek et al. | 604/307 |
| 5,012,801 A * | 5/1991 | Feret | 602/52 |
| 5,064,422 A * | 11/1991 | Wick | 604/307 |
| 5,413,567 A * | 5/1995 | Barth et al. | 604/307 |
| 5,540,922 A * | 7/1996 | Fabo | 424/402 |
| 5,755,681 A * | 5/1998 | Plews | 602/58 |
| 5,891,076 A * | 4/1999 | Fabo | 602/52 |
| 6,479,724 B1 * | 11/2002 | Areskoug et al. | 602/41 |
| 6,607,799 B1 * | 8/2003 | Heinecke et al. | 428/40.1 |
| 6,685,682 B1 * | 2/2004 | Heinecke et al. | 604/307 |
| 6,984,427 B2 * | 1/2006 | Galkiewicz et al. | 428/40.1 |
| 7,531,711 B2 * | 5/2009 | Sigurjonsson et al. | 602/54 |
| 7,902,420 B2 * | 3/2011 | Kase | 602/55 |
| 2003/0017291 A1 * | 1/2003 | Fleming et al. | 428/40.1 |
| 2005/0193609 A1 * | 9/2005 | Schwartz | 40/638 |
| 2008/0114278 A1 * | 5/2008 | Fabo et al. | 602/48 |

FOREIGN PATENT DOCUMENTS

| | | |
|---|---|---|
| EP | 0481939 | 4/1992 |
| EP | 0 562 448 A1 | 9/1993 |
| JP | 7-2653 | 4/1992 |
| JP | 2005-171030 A | 6/2005 |
| JP | 2005171030 A * | 6/2005 |
| WO | 00/26003 A1 | 5/2000 |
| WO | WO 02/74877 | 9/2002 |
| WO | 2006/075950 A1 | 7/2006 |

OTHER PUBLICATIONS

Office Action issued on Dec. 7, 2011 for CN Pat. App. No. 200780013001.8, national phase of Intl. App. No. PCT/SE2007/050149, filed on Mar. 14, 2007 (Inventor—Fabo et al.; Applicant—Mölnlycke Health Care AB; pp. 1-7).

International Preliminary Report on Patentability issued Oct. 14, 2008 for International Patent Application No. PCT/SE2007/050149, which was filed Mar. 14, 2007 (Inventor—Tomas Fabo; Applicant—Molnlycke Health Care AB) (pp. 1-5).

International Search Report and Written Opinion issued Jul. 13, 2007 for International Patent Application No. PCT/SE2007/050149, which was filed Mar. 14, 2007 (Inventor—Tomas Fabo; Applicant—Molnlycke Health Care AB) (pp. 1-8).

Extended European search report issued by the European Patent Office on May 22, 2013 for European Patent Application No. 07716118.0 filed on Mar. 14, 2007 (Applicant—Mölnlycke Health Care AB // Inventors—Fabo, et al.) (5 pages).

* cited by examiner

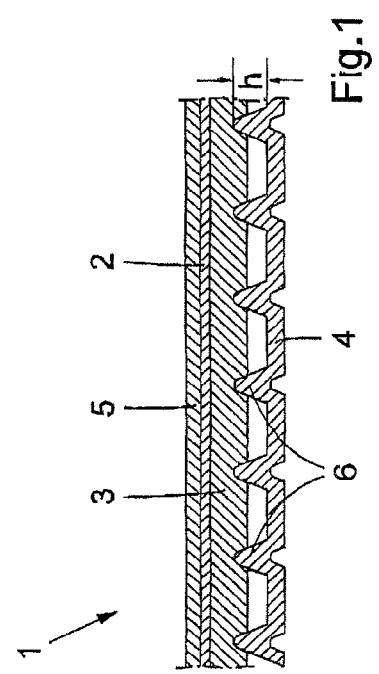
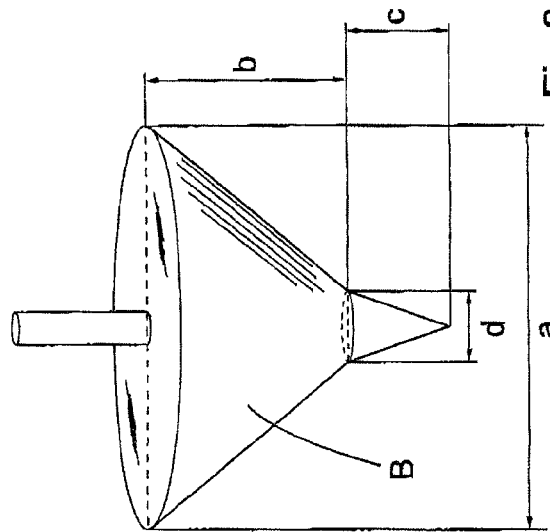
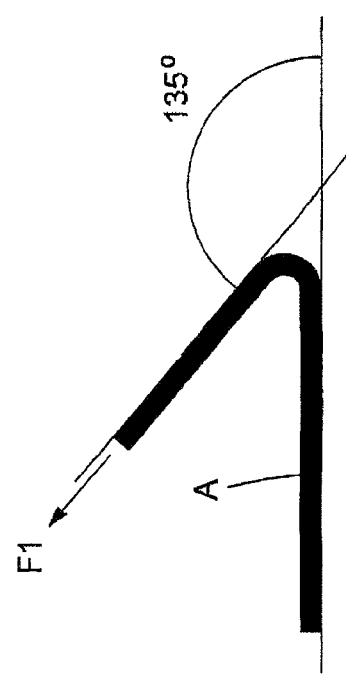
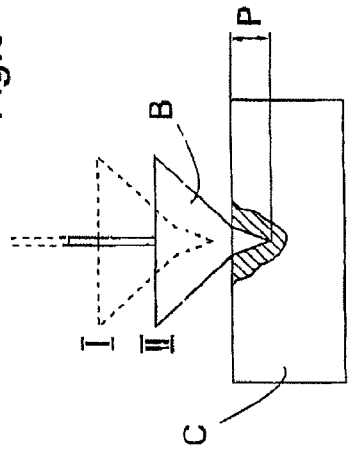

ARTICLE OR COMPONENT OF A MEDICAL AND TECHNICAL NATURE FOR AFFIXING A MEDICAL ARTICLE OR PART THEREOF TO SKIN, PROVIDED WITH A RELEASABLE PROTECTION LAYER

TECHNICAL FIELD

The present invention relates to an article or component of a medical and technical nature for affixing a medical article or part thereof to skin, which article or component comprises a layer of carrier material that has a layer of a soft skin-friendly adhesive on one side, and a protection layer that protects the adhesive layer before use of the dressing and is affixed to the adhesive layer in such a way that it is releasable.

BACKGROUND ART

Dressings for wounds provided with an adhesive layer that affixes the dressing to a user's skin are provided before use with a protection layer over the adhesive layer, partly in order to make the dressing easier to handle and partly in order to prevent, for example, dust adhering to the adhesive layer and hence reducing its adhesion. Traditionally, such protection layers have consisted of silicone-coated paper, so-called release paper, that has little adhesion to the adhesives that are traditionally used on dressings. Recently, the use of soft skin-friendly adhesives, primarily silicone-based adhesives, has increased. For such adhesives, silicone-coated paper does not work so well, as the adhesion between the silicone-based adhesive and the silicone coating on the paper is too strong. A plastic film is therefore often used as a protection layer for dressings provided with soft skin-friendly adhesive. Silicone-based adhesive can also be found on other products for affixing medical articles or the like to skin. Examples of such products are colostomy bags, fixing tape for tubes, surgical drapes or surgical instruments.

In order to reduce the adhesion of plastic films to adhesive layers on, for example, sanitary towels, a known method is to provide such a layer with a pattern of projections so that the contact surface between the film and the adhesive layer is reduced. JP 2005-171 030 shows a splicing tape with a silicone-based adhesive and a protection layer provided with a pattern of projections with a triangular or hemispherical cross section. Surprisingly, however, for dressings with very thin and flexible layers of carrier material and very soft adhesive, it has been found that the adhesion between a protection layer provided with projections and the adhesive layer increases considerably with time, and can sometimes even be stronger than for a protection layer without projections instead of being weaker, which was, after all, the intention of using a protection layer provided with projections.

It has also been found to be difficult to achieve an effective sterilization with ethylene oxide gas of dressings and other medical articles provided with soft skin-friendly adhesive and a protection layer of plastic film, irrespective of whether the protection layer was provided with projections or not.

The object of the present invention is to achieve an article of a medical and technical nature intended to be affixed to skin, or a component for affixing a medical article or a part thereof to skin, provided with a protection layer, with the adhesion between the protection layer and the article or component not being changed to any great extent when subjected to pressure and with an effective sterilization being able to be carried out by means of ethylene oxide gas.

DISCLOSURE OF INVENTION

This object is achieved according to the invention by means of an article of a medical and technical nature intended to be affixed to skin, or a component for affixing a medical article or part thereof to skin, which article or component comprises a layer of carrier material that has a layer of a soft skin-friendly adhesive on one side, and a protection layer that protects the adhesive layer before use of the article or component and is affixed to the adhesive layer in such a way that it can be released, characterized in that the protection layer is provided with a pattern of projections on the side facing towards the adhesive layer and in that a releasable reinforcing layer is arranged on the layer of carrier material on the side opposite to the side that has the layer of skin-friendly adhesive. By the application of a reinforcing layer, it has been found that there is little difference in the adhesion between the adhesive layer and the protection layer before and after the application of pressure. The reinforcing layer also helps to prevent the edges of the layer of carrier material and the adhesive layer from rolling up as a result of external forces.

In a preferred embodiment, the reinforcing layer extends over at least a peripheral area of the layer of carrier material, but it can also extend over essentially the whole of the layer of carrier material. The adhesive has preferably a softness of 8-22 mm and the projections in the pattern of projections on the protection layer have a height that is equal to or greater than the thickness of the adhesive layer. The protection layer consists preferably of polyethylene.

The reinforcing layer can consist of or comprise a layer of paper or can consist of a purely plastic film or a plastic laminate. The layer of carrier material can consist of a plastic film.

BRIEF DESCRIPTION OF DRAWINGS

The invention will now be described with reference to the attached drawings, in which:

FIG. 1 shows schematically a cross-sectional view of a dressing according to a first embodiment of the invention, FIG. 2 illustrates a method of measuring adhesion, FIGS. 3 and 4 illustrate a method of measuring softness, FIGS. 5a,b illustrate schematically the commencement of edge rolling.

MODES FOR CARRYING OUT THE INVENTION

Figure 5A:
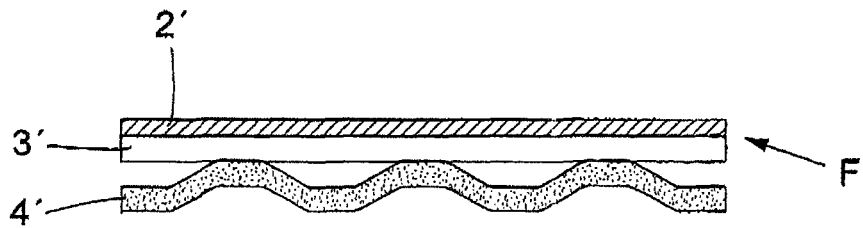
Figure 5B:
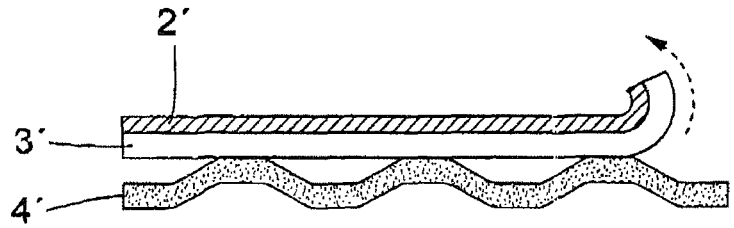

FIG. 1 shows a part of a dressing 1, that consists of a layer of carrier material 2 upon which is applied a layer 3 of soft skin-friendly adhesive. In addition, a protection layer 4 is affixed to the adhesive layer 3 in such a way that it can be released. In addition, a reinforcing layer 5 is affixed to the layer of carrier material 2 on the opposite side to the soft skin-friendly adhesive. This layer consists of plastic film (for example polypropylene or polyethylene), paper or plastic-coated paper (for example polyethylene-coated paper). If required, the reinforcing layer can consist of a transparent plastic layer.

As shown in FIG. 1, the protection layer 4 comprises a pattern of projections 6 facing towards the adhesive layer 3 and slightly indented into this. The sum of the surfaces of the projections that are surrounded by adhesive constitutes the total surface that is in contact with the adhesive and that determines the force that is required to remove the protection layer before use. The protection layer 4 should have a layer of plastic on the side facing towards the adhesive layer 3. The protection layer 4 can suitably consist in its entirety of a polyolefin plastic, for example polypropylene or polyethylene, but it is also possible to have a laminate of plastic and another material, for example paper, and other plastics, for example PVC, are also possible.

The carrier material consists of a thin plastic film, preferably of polyurethane plastic with a thickness of less than 50 micrometers, preferably 10-30 micrometers.

In addition, the adhesive in the coating must be skin-friendly and must enable the dressing to be removed without damaging the skin. This requirement is a great problem with the types of pressure-sensitive adhesives that are currently used as adhesive coatings for wound dressings. Such adhesives often adhere to the skin so firmly that parts of the Stratum Corneum, that is the upper layer of the skin, adheres to the adhesive and is pulled off from the skin when the dressing is removed. This can result in irritation and damage to the skin, especially for patients with sensitive skin, in particular elderly patients, children under the age of 3 and patients with certain illnesses, such as eczema, or undergoing certain treatments, such as cortisone treatment.

An example of a soft skin-friendly adhesive is the silicone elastomer Silgel 612 from Wacker Chemie GmbH, Germany. The silicone elastomer is very soft and has a low surface tension so that it flows into the irregularities of the skin and creates a large contact surface between the skin and the silicone elastomer. This large contact surface enables the silicone elastomer to adhere well to the skin in spite of the fact that the adhesion of the silicone elastomer to skin is not very strong. The adhesion constitutes a measurement of the energy that is required to separate/remove the adhesive layer from skin. A contributory factor to a lot of energy and hence a high traction force being required in order to remove the silicone elastomer from the skin in spite of its relatively weak adhesion is that a lot of energy is required to stretch the soft silicone elastomer before it comes loose from the skin. The softer and thicker the layer of silicone elastomer, the more energy/force is required to remove the elastomer from the skin.

If a harder adhesive is used, a stronger adhesion is required in order for the removal force to be as great as with a softer adhesive. A strong adhesion between the skin and the adhesive can easily result in skin cells being removed from the skin when the adhesive is removed.

Another disadvantage of a harder adhesive is that, with time, these can flow and thereby increase the contact surface with the skin, which means that the removal force increases with time, which can result in such adhesives becoming more difficult to remove from the skin with time. In contrast to harder adhesives, softer adhesives such as silicone elastomers achieve their full adhesion straight away so that the force required to remove them remains constant over time.

As the characteristics of the skin vary from person to person, the adhesion of the adhesive coating to the skin of different patients naturally also varies. The adhesion is also dependent upon the thickness of the soft adhesive and upon the mechanical characteristics of the layer of carrier material. The standard methods for measuring adhesion that are in use today utilize plates of different types, for example of steel or glass, and do not give values that are relevant for measuring adhesion to skin. The values for adhesion to skin of an adhesive that are stated below are to be measured by a method that is illustrated schematically in FIG. 2 and that has been developed by the applicant.

Strips of a self-adhesive dressing, the adhesion to skin of which is to be measured, are cut to a size of 25×125 mm. It should be noted that all the strips are also provided with a layer of carrier material on the back of the dressing. (The function of this layer of carrier material is to stiffen up the strips during application on the skin.) Thereafter, the strips are applied to the skin on the back of healthy volunteers. The strips are gently applied with a finger and then the layer of carrier material on the back of the strips is removed. Finally, the strips are pressed against the skin for three seconds by means of a sponge made of foamed plastic (42×182 mm, thickness=48 mm) glued onto a steel plate (50×200 mm, thickness=1 mm). The compressive force is estimated to amount to 6 $kN/m^2$. The strips remain on the skin for two minutes. Thereafter, the strips are removed at a velocity of 25 mm/second and the removal force F1 is measured. The removal angle, that is the obtuse angle that is formed between the surface of the skin and the removed part of the strip, is to be 135°. The adhesion of the strip to skin consists of the average value of the force F1. Adhesives that can be used with wound dressings according to the invention must have an adhesion according to this method of at least 0.2-4 N/25 mm. The adhesion is preferably 1-2.5 N/25 mm.

Adhesives according to the present invention must have a softness that exceeds 8 mm measured by a method based on ASTM D 937 and ASTM D 51580. Certain modifications have been made that are described below. FIGS. 3 and 4 illustrate this modified method for measuring softness of an adhesive by letting a cone B with a weight of 62.5 g penetrate by gravity into a 30 mm thick sample C of the adhesive for which the softness is to be determined. The sample is produced by filling a cylindrical glass container that has an internal diameter of 60 mm and an internal height of 35-40 mm with adhesive up to a depth of 30 mm. For a silicone elastomer, a non-cured silicone prepolymer is poured into the container and is then cross-linked to an elastomer in the glass container. The cone that is used is shown in FIG. 3 and has the following dimensions: a=65 mm, b=30 mm, c=15 mm and d=8.5 mm. When carrying out the softness measuring method, the cone B is first lowered to a position I which is shown by broken lines in FIG. 4 and in which the tip of the cone just brushes the surface of the sample C. Thereafter, the cone B is released, so that it can penetrate into the sample C by the force of gravity. The number of mm that the tip of the cone B has penetrated into the sample C after 5 seconds is measured and constitutes the penetration value P, which is larger, the softer the sample. The penetration value P constitutes the measurement of softness that is used in the present invention. A penetrometer PNR 10 from Sommer & Runge KG, Germany is used for carrying out the method.

The adhesive layer 3 in the dressing according to FIG. 1 consists of an addition-cured RTV (Room Temperature Vulcanizing) silicone system that, after admixture, cross-binds and forms an adhesive elastomer. Examples of RTV addition-cured silicone systems are given in EP 0 300 620 A1 which describes so-called gel-forming compositions that consist of an alkenyl-substituted polydiorganosiloxane, an organosiloxane containing hydrogen atoms linked to some of the silicone atoms, and also a platinum catalyst.

Wacker SilGel 612 is a commercially available RTV silicone system. This is a two-component system. The softness and degree of adhesion of the elastomer which is formed can be varied by varying the proportions of the two components A:B from 1.0:0.7 to 1.0:1.3.

Examples of other soft silicone elastomers which adhere to dry skin are NuSil MED-6340, NuSil MED3-6300 and NuSil MED 12-6300 from NuSil Technology, Carpintieria, Ga., USA and Dow Corning 7-9800 from Dow Corning Corporation, Midland, USA.

Other soft skin-friendly adhesives can also be used with the present invention, for example thermal adhesives such as Dispomelt® 70-4647 from National Starch and Chemical Company, Bridgewater, N.J., USA.

Surprisingly, for dressings provided with a flexible layer of carrier material and a layer of soft skin-friendly adhesive and with a polyethylene film provided with a pattern of projections as a protection layer, it has been found that the force that is required to remove the protection layer from the dressing increases with time and can even be greater than if a flat protection layer without projections had been used. The only logical explanation for such an increased adhesion between the protection layer and the wound dressing is that the total contact surface of the layer provided with a pattern of projections must be greater than the contact surface of the flat layer. This could have occurred as a result of the unit of carrier and adhesive assuming a shape that was complementary to the pattern of projections. Such a modifying of the shape of the unit of layer of carrier material and adhesive layer takes place completely or partially during handling of the wound dressing after manufacture, that is during packaging, storage and transportation of dressings and/or during sterilization of the dressing by means of ethylene oxide gas, during which the dressing is subjected to extreme changes in pressure. Depending upon the degree of exposure to external forces during handling, storage, transportation and sterilization, such a modifying of the shape takes place to a greater or lesser extent.

The increase in the adhesion between the protection layer and the adhesive layer brought about by the abovementioned modifying of the shape is thus dependent upon external forces and can therefore vary considerably between different dressings. Such a difference between different dressings in the force required to remove the protection layer is not desirable. Even if it remains below the limit for the maximal removal force, the removal force should not vary to any great extent between different dressings. In addition, apart from the sterilization pressure, the external forces on the dressing are localized, which results in the removal force also varying locally within the dressing.

In order to prevent the abovementioned modifying of the shape of the wound dressing to match the shape of the layer 4 that is provided with projections 6, a reinforcing layer 5 is arranged on the layer of carrier material 2 and is affixed to this on the side opposite to the side that has the adhesive layer 3, in such a way that it can be released. This means that, as a result of the rigidity of the layer 5 that is attached to the layer of carrier material 2, the layer of carrier material 2 is prevented from locally modifying its shape to match the shape of the layer 4 provided with projections in the event of an external localized force but can only move with the more rigid layer 5 and follow any curvature or bend in this in the event of a localized force and also follow its return to a flat shape when the force ceases.

It has been found that the reinforcing layer 5 does not need to extend over the whole of the layer of carrier material 2, but that it is sufficient for the layer 5 to extend around the peripheral area of the layer of carrier material 2, that is to form a frame around a central area that does not have the reinforcing layer. It is true that such a design means that the unit of carrier material and adhesive layer located in the central area can be bent and stretched locally to assume a complementary shape to that of the protection layer 4 in the event of a localized force, but as soon as the localized force ceases, the unit of carrier material and adhesive layer will return to a flat shape to even out the stresses that arise in the carrier material as a result of the abovementioned bending and stretching of the carrier material and the adhesive layer. Without the addition of the reinforcing layer 5, the stresses that arise as a result of localized indentation of the carrier material and the adhesive layer would be directly equalized by localized movement of the carrier material and adhesive in relation to the protection layer. As a result of the reinforcing layer 5 being affixed to the carrier material, such a localized movement is prevented and remaining stresses in the carrier material and in the adhesive layer are equalized by this layer reassuming its flat shape after the force ceases.

An additional advantage of the application of the reinforcing layer 5 is that it prevents the edges of the dressing from rolling up. A dressing without a reinforcing layer and with a layer of carrier material 2', an adhesive layer 3' and a protection layer 4' that is subjected to a force F directed towards the edge of the dressing is shown schematically in FIGS. 5a,b. The force F can arise as a result of shaking of the packaging, bending, frictional forces, etc. As a result of the edge of the layer of carrier material 2' and the adhesive 3' not being attached to the more rigid protection layer 4', the "free edge" of the layers 2', 3' is bent by the force F and thereby becomes attached to the surroundings, that is to the surrounding packaging. This applies, in particular, if the projections consist of linear ridges with a longitudinal extent perpendicular to the plane of the paper. If a reinforcing layer 5 is arranged over the layer 2', the dressing can largely withstand the edge-rolling forces.

The reinforcing layer 5 does not, of course, remain on the dressing in use, but is removed before or in association with the application of the dressing on a patient. The adhesion between the layer 5 and the layer of carrier material 2 must therefore be less than the adhesion of the adhesive 3 to skin, so that the dressing remains affixed to the skin when the reinforcing layer 5 is removed after the dressing has been applied. The attachment between the layer of carrier material 2 and the reinforcing layer 5 can consist of an adhesive attachment, but can also be achieved in other ways, for example by combined extrusion if both layers consist of plastic material or by heating up one or both layers to a semi-molten state, for example by thermal lamination via rollers.

The use of the reinforcing layer 5 thus ensures that the dressing 1, that is the unit of layer of carrier material 2 and layer of adhesive 3, will be a certain distance from the base of the protection layer 4, from which base the projections 6 project towards the dressing. As a result of this, during sterilization with ethylene oxide gas or other gas, the gas has free access to the surface of the adhesive layer via the system of channels that is formed between the projections in the pattern of projections. This means that the sterilization process is much more effective than for dressings without a pattern of projections and, as a result, it can be carried out more quickly. The reinforcing layer also ensures that the adhesion between the protection layer and the adhesive layer is kept at the intended level irrespective of external forces during the production process, including packaging, during sterilization, transportation, storage and in association with application.

It will be recognized that the softer the adhesive, the greater the extent to which the projections can be indented into the adhesive layer in the event of an external force. In order to ensure that the handling of the dressing does not result in the projections being pressed completely into the adhesive layer 3, the projections 6 can be given a height h, that is the extent that the projections project beyond the protection layer 4, that exceeds the thickness of the adhesive layer 3.

In order to measure the effect of the reinforcing layer, delaminating tests were carried out with four different samples A-D, with A consisting of a sample constructed of a layer of carrier material and an adhesive layer provided with a protection layer that has a pattern of projections, B consisting of a similar material provided with a reinforcing layer on its upper side, C consisting of a sample according to A but with a flat protection layer and D consisting of a sample according to B but with a flat protection layer. The different protection layers or release layers were applied manually and the tests were carried out one week after the application of the release layers.

The test was carried out in the following way. Firstly, samples of size 25×200 mm were cut from a material A-D as described above. The layer of carrier material in the material A-D consisted of 20 μm polyurethane film, 4200 Z-T, Epurex Films GmbH, Walsrode, Germany and the adhesive layer consisted of SilGel 612 with a softness of 14-15 mm. For the samples A and B, 90 μm thick embossed LDPE 16000, with embossing 124 from Huthamaki, Forchheim, Germany was used as the protection layer or release layer and, for samples C and D, 100 μm thick smooth LDPE 16000 from the same company was used as the protection layer or release layer. The samples B and D were also provided with a reinforcing layer over the layer of carrier material, which reinforcing layer consisted of 120 g/m² paper coated with 15 g/m² PE, Polyguard E MG 120/PE15 Treat 30+, Amcor Flexibles, Lund, Sweden.

In a first test cycle (A1-D1), a delamination test was carried out straight away, as described below.

The test was carried out in the following way. A piece of the release layer was removed from the adhesive-coated surface, at one end of the laminate. The release layer was held in the upper clamp of the tensile tester (Alliance RT/1 or equivalent) and the adhesive-coated laminate was held in the lower clamp of the tensile tester. The tensile tester was started and the average force required to pull the release layer from the silicone-coated surface of the sample was recorded. The tensile tester moved with a velocity of 42 mm/second. During the measurement of the force, the non-delaminated part of the laminate was held straight, so that both the angles that were formed between the two clamped parts and the non-delaminated part of the laminate were approximately 90°.

In a second cycle (A2-D2), the delamination test was not carried out until after the two cut-out samples of 25×200 mm in size had been subjected to a load by a rolling method as described below. The samples were placed on a flat base with a piece of polyurethane foam (1.6 mm L00562-5 from Rynel Inc., Boothbay, Me., USA) over the sample. The samples were then subjected to a load by a roller (45 mm wide, weight=2 kg, r=47 mm) being rolled once forward and back over the piece of foam at a velocity of 5 mm/second. The samples were then tested immediately after the rolling, without a waiting period.

The test was carried out with two different surface weights of the adhesive layer, 60 and 100 g/m², for each material A-D.

Figure 6:
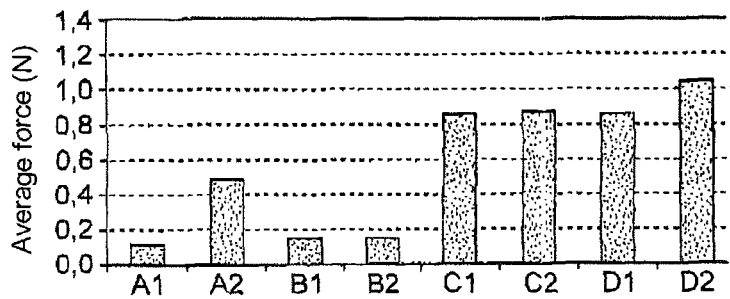
FIGS. 6 and 7 show bar charts of the delaminating force between the release material and the adhesive for test samples with adhesive layers of different thicknesses and with different release materials.
Figure 7:
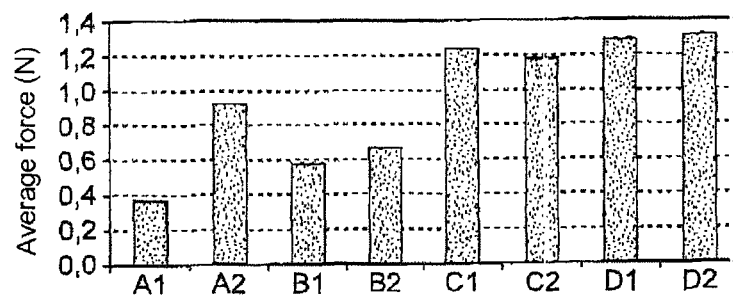

The results of the tests are shown in FIGS. 6 and 7 and in Tables 1 and 2.

TABLE 1

| 60 gsm silicone | Sample | | | | | | | |
|---|---|---|---|---|---|---|---|---|
| | A1 | A2 | B1 | B2 | C1 | C2 | D1 | D2 |
| Average value (N/25 mm): | 0.10 | 0.49 | 0.15 | 0.14 | 0.86 | 0.87 | 0.86 | 1.04 |
| Std dev. | 0.01 | 0.06 | 0.04 | 0.03 | 0.02 | 0.02 | 0.07 | 0.17 |

TABLE 2

| 100 gsm silicone | Sample | | | | | | | |
|---|---|---|---|---|---|---|---|---|
| | A1 | A2 | B1 | B2 | C1 | C2 | D1 | D2 |
| Average value (N/25 mm): | 0.37 | 0.92 | 0.57 | 0.66 | 1.22 | 1.17 | 1.27 | 1.30 |
| Std. dev. | 0.07 | 0.05 | 0.13 | 0.11 | 0.02 | 0.03 | 0.07 | 0.03 |

As shown in the tables and in the figures, there was a considerable difference between the delaminating forces for the different materials A-D before and after subjecting them to a load for the samples of material A, that is the embossed protection layer on material without a reinforcing layer, while for the materials B and C, there was little difference. It is difficult to explain the value in FIG. 6 for the material D after it was subjected to a load, and the difference between the values D1 and D2 in FIG. 6 could be due to the protection layer on the material for D1 not having been applied properly on the adhesive layer. The C and D materials are, however, only included in the test as reference material, for which reason the difference does not need to be investigated further.

The increase in the delaminating force in Table 1 for the material A=A2−A1=0.39, which gives an increase of 390%, while the increase for the material B=B2−B1=−0.1, that is, no increase at all.

The increase in the delaminating force in Table 2 for the material A=0.55, which gives an increase of approximately 149%. For the material B, the increase is 0.09, which is an increase of approximately 16%.

In order to ensure that the material functions well, the increase after it has been subjected to a load should not exceed 50%, and should preferably not exceed 30%. In addition, the delaminating force should preferably be less than 0.8 N, more preferably 0.7 N, in order for the dressing to work well.

In addition, it is possible to reduce the ability of the projections to penetrate into the adhesive layer by giving the tops of the projections a rounded or even a flat shape. It is also possible to design the tops of the projections with a tip that can penetrate easily into the adhesive, which tip is surrounded by a circular surface that has a great resistance to penetrating.

The embodiment that is described above can, of course, be modified within the framework of the invention. For example, the pattern of projections on the protection layer can be non-homogenous; for example, they can be sparser on the part at which the removal of the protection layer commences. In addition, the shape of the projections can be different, for example they can be cylindrical, hemispherical, cubical, etc. Nor do the projections need to be in the form of individual points but can be in the form of lines. Linear projections can have any curved shape, for example they can be the shape of a sine wave. The reinforcing layer does not necessarily need to extend right out to the periphery of the layer of carrier material, but parts or even all of the peripheral area can be without a reinforcing layer. The invention is therefore only limited by the content of the attached claims.

The invention claimed is:

1. An article of a medical and technical nature intended to be affixed to skin, or a component for affixing a medical article or part thereof to skin, which article or component comprises:
    a layer of carrier material that has a layer of a soft skin-friendly adhesive on one side, wherein the adhesive has a softness of 8-22 mm; and
    a protection layer that protects the adhesive layer before use of the article or component and is affixed to the adhesive layer in such a way that it is releasable, wherein the protection layer comprises a base and a pattern of projections on the side facing towards the adhesive layer, said pattern of projections extending from the base toward the adhesive layer, wherein the projections in the pattern of projections on the protection layer have a height that is greater than a thickness of the adhesive layer such that the base of the protection layer is spaced from the adhesive layer, and wherein a reinforcing layer is arranged on the layer of carrier material, on the opposite side to the side that has the layer of soft skin-friendly adhesive, in such a way that it can be removed.

2. The article or component of claim 1, wherein the reinforcing layer extends over at least a peripheral area of the layer of carrier material.

3. The article or component of claim 2, wherein the reinforcing layer extends over essentially the whole of the layer of carrier material.

4. The article or component of claim 1, wherein the increase in the removal force (B2−B1) after the application of a load of 2 kg on the component by means of a rolling method is less than 50%.

5. The article or component of claim 4, wherein the force required to remove the protection layer is less than or equal to 0.8 N/25 mm.

6. The article or component of claim 1, wherein the protection layer consists of a polyolefin plastic.

7. The article or component of claim 6, wherein the protection layer consists of polyethylene.

8. The article or component of claim 6, wherein the reinforcing layer comprises a layer of paper.

9. The article or component of claim 6, wherein the reinforcing layer consists of a plastic material.

10. The article or component of claim 6, wherein the layer of carrier material consists of a plastic film.

11. The article or component of claim 6, wherein the layer of carrier material consists of a flexible plastic film that has a thickness of less than 50 μm.

12. The article or component of claim 7, wherein the reinforcing layer comprises a layer of paper.

13. The article or component of claim 7, wherein the reinforcing layer consists of a plastic material.

14. The article or component of claim 1, wherein the increase in the removal force (B2−B1) after the application of a load of 2 kg on the component by means of a rolling method is less than 30%.

15. The article or component of claim 4, wherein the force required to remove the protection layer is less than or equal to 0.2 N/25 mm.

16. The article or component of claim 6, wherein the layer of carrier material consists of a flexible plastic film that has a thickness of 10-30 μm.

17. The article or component of claim 1, wherein the reinforcing layer is in the form of a frame.

18. The article or component of claim 1, wherein the soft skin-friendly adhesive comprises a silicone elastomer.

* * * * *

UNITED STATES PATENT AND TRADEMARK OFFICE
CERTIFICATE OF CORRECTION

PATENT NO. : 8,530,022 B2  Page 1 of 1
APPLICATION NO. : 12/296314
DATED : September 10, 2013
INVENTOR(S) : Fabo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 509 days.

Signed and Sealed this
Fifteenth Day of September, 2015

Michelle K. Lee
*Director of the United States Patent and Trademark Office*